US011207424B2

(12) United States Patent
Ikeda et al.

(10) Patent No.: US 11,207,424 B2
(45) Date of Patent: Dec. 28, 2021

(54) METHODS AND MATERIALS FOR INCREASING VIRAL VECTOR INFECTIVITY

(71) Applicants: Mayo Foundation for Medical Education and Research, Rochester, MN (US); University of Pittsburgh—Of the Commonwealth System of Higher Education, Pittsburgh, PA (US)

(72) Inventors: Yasuhiro Ikeda, Rochester, MN (US); Claire A. Schreiber, Rochester, MN (US); Toshie Sakuma, Rochester, MN (US); Sara J. Holditch, Rochester, MN (US); Kazunori Koide, Pittsburgh, PA (US)

(73) Assignees: Mayo Foundation for Medical Education and Research, Rochester, MN (US); University of Pittsburgh—Of the Commonwealth System of Higher Educat, Pittsburgh, PA (US)

( * ) Notice: Subject to any disclaimer, the term of this patent is extended or adjusted under 35 U.S.C. 154(b) by 0 days.

(21) Appl. No.: 15/318,618

(22) PCT Filed: Jun. 12, 2015

(86) PCT No.: PCT/US2015/035639
§ 371 (c)(1),
(2) Date: Dec. 13, 2016

(87) PCT Pub. No.: WO2015/192063
PCT Pub. Date: Dec. 17, 2015

(65) Prior Publication Data
US 2017/0112946 A1 Apr. 27, 2017

Related U.S. Application Data

(60) Provisional application No. 62/012,145, filed on Jun. 13, 2014.

(51) Int. Cl.
| C12N 15/864 | (2006.01) |
| A61K 48/00 | (2006.01) |
| C12N 15/09 | (2006.01) |
| C12N 15/86 | (2006.01) |
| A61K 31/5377 | (2006.01) |
| A61K 38/00 | (2006.01) |

(52) U.S. Cl.
CPC .......... *A61K 48/00* (2013.01); *A61K 31/5377* (2013.01); *A61K 48/0083* (2013.01); *C12N 15/86* (2013.01); *A61K 38/00* (2013.01); *C12N 2750/14143* (2013.01)

(58) Field of Classification Search
None
See application file for complete search history.

(56) References Cited

U.S. PATENT DOCUMENTS

| 7,988,957 B2 | 8/2011 | Okada et al. |
| 2008/0199438 A1 | 8/2008 | Sueishi et al. |
| 2010/0310516 A1 | 12/2010 | Samulski et al. |
| 2011/0263015 A1* | 10/2011 | D'Costa ............... C12N 5/0696 435/366 |

FOREIGN PATENT DOCUMENTS

WO    WO 2013/130882    9/2013

OTHER PUBLICATIONS

Mingozzi and High, Immune responses to AAV vectors: overcoming barriers to successful gene therapy, Blood, 2013, pp. 23-36.*
Hinderer et al, Severe Toxicity in Nonhuman Primates and Piglets Following High-Dose Intravenous Administration of an Adeno-Associated Virus Vector Expressing Human SMN, Human Gene Therapy, vol. 29, No. 3, 2018, pp. 285-298.*
Fumoto et al, Targeted Gene Delivery: Importance of Administration Routes, Chapter 1, Intech, 2013, pp. 3-31.*
Chen et al., Efficient Gene Delivery and Expression in Pancreas and Pancreatic Tumors by Capsid-Optimized AAV8 Vectors, Human Gene Therapy Methods, vol. 28 No. 1, 2017, pp. 49-59.*
Mak et al, Lost in translation: animal models and clinical trials in cancer treatment, Am J Transl Res 2014;6(2): 114-118.*
Deverman et al, Gene therapy for neurological disorders: progress and prospects, Nature Reviews Drug Discovery 17, 641-669 (2018).*
Naso et al, Adeno-Associated Virus (AAV) as a Vector for Gene Therapy, BioDrugs (2017) 31:317-334.*
AAV Vector Immunogenicity in Humans: A Long Journey to Successful Gene Transfer, Molecular Therapy vol. 28 No. 3 Mar. 2020, pp. 723-746.*
Asokan et al., "The AAV vector toolkit: poised at the clinical crossroads," *J Am Soc Gen Ther.*, 20(4):699-708, Apr. 2012.
Cataliotti et al., "Long-term cardiac pro-B-type natriuretic peptide gene delivery prevents the development of hypertensive heart disease in spontaneously hypertensive rats," *Circulation.*, 123(12):1297-1305, Mar. 29, 2011.
Effenberger et al., "Coherence between Cellular Responses and in Vitro Splicing Inhibition for the Anti-tumor Drug Pladienolide B and Its Analogs," *J Biolog Chem.*, 289(4): 1938-1947, Jan. 24, 2014.
Extended European Search Report in International Application No. EP 15806833.8, dated Nov. 3, 2017, 6 pages.
Hubert et al., "Genome-wide RNAi screens in human brain tumor isolates reveal a novel viability requirement for PHF5A," *Genes Dev.*, 27:1032-1045, 2013.

(Continued)

*Primary Examiner* — Maria Marvich
(74) *Attorney, Agent, or Firm* — Fish & Richardson P.C.

(57) ABSTRACT

This document relates to methods and materials for increasing viral vector infectivity. For example, methods and materials for using spliceosome inhibitors (e.g., U2 snRNP spliceosome inhibitors such as meayamycin B or pladienolide derivative E7107) to increase viral vector (e.g., adeno-associated virus-based vector) infectivity are provided.

4 Claims, 24 Drawing Sheets

Specification includes a Sequence Listing.

(56) References Cited

OTHER PUBLICATIONS

Rzymski et al., "PHF5A represents a bridge protein between splicing proteins and ATP-dependent helicases and is differentially expressed during mouse spermatogenesis," *Cytogenet Genome Res.*, 121:232-244, 2008.

Schneider-Poetsch et al., "Garbled messages and corrupted translations," *Nat Chem Biol.*, 6:189-198, 2010.

Schreiber et al., "An siRNA screen identifies the U2 snRNP spliceosome as a host restriction factor for recombinant adeno-associated viruses," *PLOS Pathogens.*, 11(8):e1005082, Aug. 5, 2015, 25 pages.

Schreiber et al., "Further characterization of U2 snRNP mediated restriction of AAV vector transduction," *Mol Ther.*, 24(Supplement 1):S4, May 2016, Abstract Only, 2 pages.

Takeda et al., "Successful gene transfer using adeno-associated virus vectors into the kidney: comparison among adeno-associated virus serotype 1-5 vectors in vitro and in vivo," *Nephron Exp Nephrol.*, 96(4):e119-e126, Apr. 2004.

Wang et al., "Rds3p is Required for Stable U2 snRNP Recruitment to the Splicing Apparatus," *Mol Cell Biol.*, 23(20):7339-7349, Oct. 2003.

Yang et al., "A myocardium tropic adeno-associated virus (AAV) evolved by DNA shuffling and in vivo selection," *PNAS.*, 106(10):3946-3951, Mar. 10, 2009.

Nakajima et al., "New antitumor substances, FR901463, FR901464 and FR901465. II. Activities against experimental tumors in mice and mechanism of action," *J. Antibiot.*, 49(12):1204-1211, Dec. 1996.

Salton et al., "Inhibition of vemurafenib-resistant melanoma by interference with pre-mRNA splicing," *Nat. Commun.*, 6:7103, May 2015.

Xargay-Torrent et al., "The splicing modulator sudemycin induces a specific antitumor response and cooperates with ibrutinib in chronic lymphocytic leukemia," *Oncotarget.*, 6(26):22734-22749, Sep. 2015.

Gregorevic et al., "Systemic delivery of genes to striated muscles using adenoassociated viral vectors," *Nat. Med.*, 10(8):828-834, Aug. 2004.

Inagaki et al., "Robust Systemic Transduction with AAV9 Vectors in Mice: Efficient Global Cardiac Gene Transfer Superior to That of AAV8" *Mol. Ther.*, 14(1):45-53, Jul. 2006.

Nakai et al., "Unrestricted Hepatocyte Transduction with Adeno-Associated Virus Serotype 8 Vectors in Mice," *Journal of virology*, 79(1):214-224, Aug. 2004.

\* cited by examiner

METHODS AND MATERIALS FOR INCREASING VIRAL VECTOR INFECTIVITY

CROSS REFERENCE TO RELATED APPLICATIONS

This application is a National Stage application under 35 U.S.C. § 371 of International Application No. PCT/US2015/035639, having an International Filing Date of Jun. 12, 2015, which claims the benefit of U.S. Provisional Ser. No. 62/012,145 filed Jun. 13, 2014. This disclosure of the prior application is considered part of (and is incorporated by reference in) the disclosure of this application.

STATEMENT AS TO FEDERALLY SPONSORED RESEARCH

This invention was made with government support under CA120792 awarded by National Institutes of Health. The government has certain rights in the invention.

TECHNICAL FIELD

This document relates to methods and materials for increasing viral vector infectivity. For example, this document relates to the use of spliceosome inhibitors (e.g., U2 snRNP spliceosome inhibitors such as FR901464, pladienolide B, meayamycin B, Sudemycins, E7107, and spliceostatin A) to increase viral vector (e.g., adeno-associated virus-based vector) infectivity.

BACKGROUND INFORMATION

Adeno-associated virus (AAV) is a non-enveloped, single-stranded DNA virus that belongs to the family Parvoviridae. AAV-based vectors emerged as a promising vehicle to achieve long-term gene expression with low toxicity. Recombinant vectors based on AAV serotype capsids and libraries of engineered capsid mutants demonstrated unique receptor usages and tissue tropisms, providing versatility for tissue-targeted gene expression (Asokan et al., *J. Am. Soc. Gene Ther.*, 20:699-708 (2012)). For instance, AAV vectors with AAV serotype 9 (AAV9) capsid efficiently transduce cardiac tissues, while vectors with AAV2 capsid show efficient transduction of kidney cells (Cataliotti et al., *Circulation*, 123:1297-1305 (2011); Takeda et al., *Nephron. Exp. Nephrol.*, 96:e119-126 (2004); and Yang et al., *PNAS*, 106:3946-3951 (2009)).

SUMMARY

This document provides methods and materials for increasing viral vector infectivity. For example, this document provides methods and materials for using one or more spliceosome inhibitors (e.g., meayamycin B, FR901464, pladienolide B, Sudemycins, E7107, or spliceostatin) to increase viral vector (e.g., adeno-associated virus-based vector) infectivity.

As described herein, contacting cells with one or more spliceosome inhibitors (e.g., meayamycin B, FR901464, pladienolide B, Sudemycins, E7107, or spliceostatin) before or after the cells are exposed to an AAV designed to express a polypeptide (e.g., a heterologous polypeptide) can result in increased AAV infectivity and/or increased expression of the polypeptide. In some cases, one or more spliceosome inhibitors (e.g., meayamycin B, FR901464, pladienolide B, Sudemycins, E7107, or spliceostatin) can be administered to a mammal before, together with, or after administration of an AAV designed to express a polypeptide (e.g., a heterologous polypeptide). In such cases, increased AAV infectivity or increased polypeptide expression can occur within the mammal as compared to the level of AAV infectivity or polypeptide expression that occurs in a comparable mammal in the absence of administration of the one or more spliceosome inhibitors.

Having the ability to use one or more spliceosome inhibitors to increase viral vector (e.g., adeno-associated virus-based vector) infectivity and/or the expression of nucleic acid of a viral vector (e.g., adeno-associated virus-based vector) can allow clinicians to express viral vector nucleic acids in cells within a mammal using lower viral vector doses than would be required in the absence of the one or more spliceosome inhibitors.

In general, one aspect of this document features a method for increasing adeno-associated virus vector infectivity of cells. The method comprises, or consists essentially of, contacting cells with the adeno-associated virus vector and a U2 snRNP spliceosome inhibitor. The adeno-associated virus vector can be an AAV1, AAV2, AAV3, AAV4, or AAV5 vector. The adeno-associated virus vector can be an AAV6, AAV7, AAV8, AAV9, AAVrh10, chimeric AAV, or simian AAV vector. The cells can be human islet cells. The inhibitor can be meayamycin B or E7107. The cells can be contacted with the vector prior to or at the same time as being contacted with the inhibitor. The cells can be contacted with the vector after being contacted with the inhibitor.

Another aspect of this document features a method for increasing expression of heterologous nucleic acid of an adeno-associated virus vector. The method comprises, or consists essentially of, contacting cells with the adeno-associated virus vector and a U2 snRNP spliceosome inhibitor, wherein the adeno-associated virus vector comprises nucleic acid heterologous to adeno-associated viruses, and wherein expression of the heterologous nucleic acid is increased as compared to comparable cells exposed to the adeno-associated virus vector in the absence of the inhibitor. The adeno-associated virus vector can be an AAV1, AAV2, AAV3, AAV4, or AAV5 vector. The adeno-associated virus vector can be an AAV6, AAV7, AAV8, AAV9, AAVrh10, chimeric AAV, or simian AAV vector. The cells can be human islet cells. The inhibitor can be meayamycin B or E7107. The cells can be contacted with the vector prior to or at the same time as being contacted with the inhibitor. The cells can be contacted with the vector after being contacted with the inhibitor. The heterologous nucleic acid can encode a human polypeptide.

Another aspect of this document features a method for increasing adeno-associated virus vector infectivity of cells within a mammal. The method comprises, or consists essentially of, administering the adeno-associated virus vector and a U2 snRNP spliceosome inhibitor to the mammal. The mammal can be a human. The adeno-associated virus vector can be an AAV1, AAV2, AAV3, AAV4, or AAV5 vector. The adeno-associated virus vector can be an AAV6, AAV7, AAV8, AAV9, AAVrh10, chimeric AAV, or simian AAV vector. The cells can be human islet cells. The inhibitor can be meayamycin B or E7107. The vector can be administered to the mammal prior to the inhibitor is administered to the mammal. The inhibitor can be administered to the mammal prior to the vector is administered to the mammal. The inhibitor and the vector can be administered to the mammal together or at the same time.

Another aspect of this document features a method for increasing expression of heterologous nucleic acid of an adeno-associated virus vector in cells present within a mammal. The method comprises, or consists essentially of, administering the adeno-associated virus vector and a U2 snRNP spliceosome inhibitor to the mammal, wherein the adeno-associated virus vector comprises nucleic acid heterologous to adeno-associated viruses, and wherein expression of the heterologous nucleic acid is increased as compared to comparable cells from a mammal administered the adeno-associated virus vector in the absence of the inhibitor. The mammal can be a human. The adeno-associated virus vector can be an AAV1, AAV2, AAV3, AAV4, or AAV5 vector. The adeno-associated virus vector can be an AAV6, AAV7, AAV8, AAV9, AAVrh10, chimeric AAV, or simian AAV vector. The cells can be human islet cells. The inhibitor can be meayamycin B or E7107. The vector can be administered to the mammal prior to the inhibitor is administered to the mammal. The inhibitor can be administered to the mammal prior to the vector is administered to the mammal. The inhibitor and the vector can be administered to the mammal together or at the same time. The heterologous nucleic acid can encode a human polypeptide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
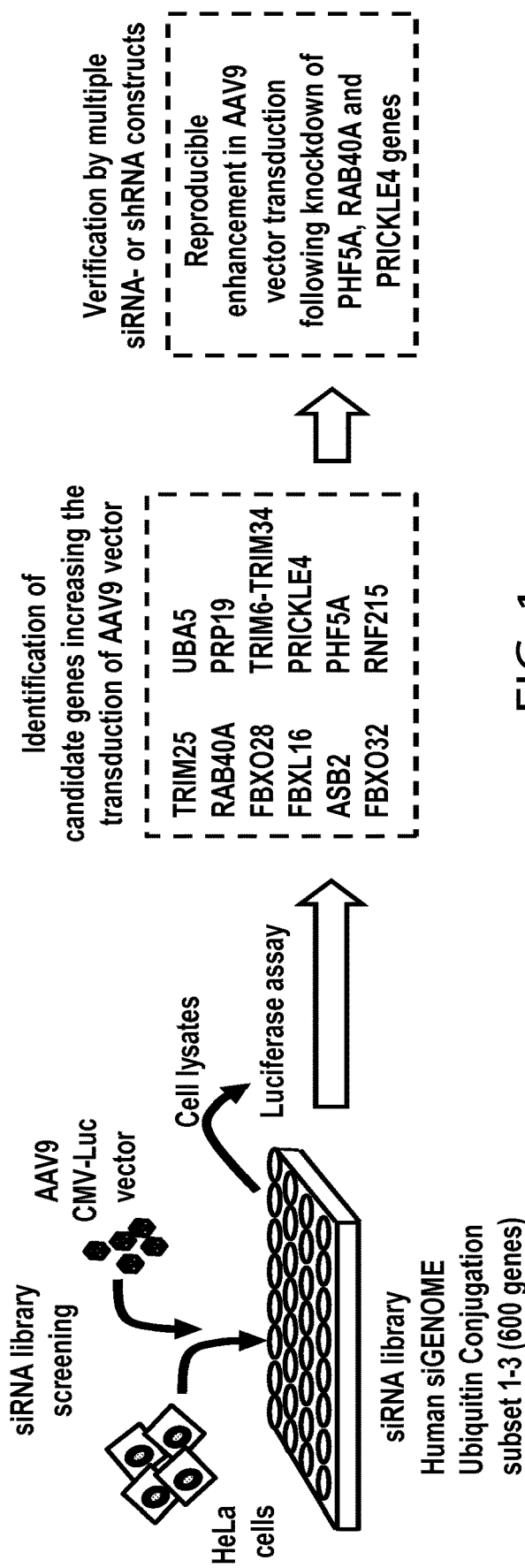
FIG. 1 contains the schematic representation of screening of the siRNA library. Screening was carried out by reverse transfection of HeLa cells with siRNAs, followed by infection with luciferase-expressing AAV9 vectors (AAV9 CMV-Luc), and assessment of luciferase expression. Screening of the library identified 12 candidate genes that increased transduction by AAV9 vectors over 10-fold. Further studies were carried out in HeLa cells transfected/transduced with specific siRNAs or shRNA lentivectors for each of the 12 genes to verify the screening candidates.

This document provides methods and materials for increasing viral vector infectivity. For example, this document provides methods and materials for using one or more spliceosome inhibitors (e.g., meayamycin B, FR901464, pladienolide B, Sudemycins, E7107, or spliceostatin) to increase viral vector (e.g., adeno-associated virus-based vector) infectivity.

As described herein, contacting cells (e.g., in vitro, ex vivo, or in vivo) with one or more spliceosome inhibitors (e.g., a U2 snRNP spliceosome inhibitor such as an inhibitor of PHF5A) before or after the cells are exposed to a viral vector (e.g., an AAV vector) designed to express a polypeptide (e.g., a heterologous polypeptide) can result in increased viral vector infectivity and/or increased expression of the polypeptide. Examples of spliceosome inhibitors that can be used as described herein include, without limitation, FR901464, pladienolide B, meayamycin B, Sudemycins, E7107, and spliceostatin A. In some cases, cells to be infected with a viral vector can be exposed to one or more spliceosome inhibitors (e.g., meayamycin B, FR901464, pladienolide B, Sudemycins, E7107, or spliceostatin) before (e.g., no more than about one day, 12 hours, eight hours, six hours, four hours, two hours, one hour, 30 minutes, 15 minutes, five minutes, or one minute before) being exposed to the viral vector. In some cases, cells to be infected with a viral vector can be exposed to one or more spliceosome inhibitors (e.g., meayamycin B, FR901464, pladienolide B, Sudemycins, E7107, or spliceostatin) after (e.g., no more than about 12 hours, eight hours, six hours, four hours, two hours, one hour, 30 minutes, 15 minutes, five minutes, or one minute after) being exposed to the viral vector. In some cases, cells to be infected with a viral vector can be exposed to one or more spliceosome inhibitors (e.g., meayamycin B, FR901464, pladienolide B, Sudemycins, E7107, or spliceostatin) at the same time as being exposed to the viral vector.

Examples of viral vectors that can be used as described herein include, without limitation, any appropriate AAV vector such as AAV1, AAV2, AAV3, AAV4, AAV5, AAV6, AAV7, AAV8, AAV9, AAVrh10, or other generations of AAV vectors with hybrid/chimeric AAV capsids among AAV serotypes, or AAV capsids with additional mutations. A viral vector used as described herein can include heterologous nucleic acid that encodes a heterologous polypeptide. For example, an AAV viral vector used as described herein can include nucleic acid that encodes a polypeptide such as a clotting factor (e.g., factor IX), a neuronal trophic factor (e.g., GNDF), a beta cell trophic factor (e.g., GLP-1 and betatrophin), an hepatocyte-trophic factor (e.g., HGF), a natriuretic peptide (e.g., b-type natriuretic peptide and atrial natriuretic peptide), a hormone (e.g., thyrotropin-releasing hormone, vasopressin, growth hormone, follicle-stimulating hormone, thyroid-stimulating hormone, renin, angiotensin, uromodulin, klotho, urodilatin, or erythropoietin), glutamic acid descarboxylase, an immuno-modulatory factor (e.g., CTLA4-Ig, PD1, and PDL1), dystrophin, an anti-apoptotic factor (e.g., Bcl-2), an apoptosis-inducing polypeptide (e.g., caspase 3, 7, and 6), an anti-ER/oxidative stress factor (e.g., SOD1). In some cases, a viral vector provided herein can be designed to induce immune responses within a mammal and/or to treat cancer. For example, an AAV vector can be designed to drive expression of a cancer immunogen or a viral antigen. In some cases, a viral vector that can be used as described herein can be designed to deliver gene editing enzymes and donor sequences within a mammal. For example, an AAV vector can be designed to deliver a gene editing enzyme (e.g., Cas9) to cleave specific DNA sequences. In some cases, a viral vector (e.g., an AAV vector) that can be used as described herein can be administered to a mammal to deliver an encoded nuclease for gene editing.

Any appropriate cell can be exposed to both a viral vector and one or more spliceosome inhibitors (e.g., meayamycin B, FR901464, pladienolide B, Sudemycins, E7107, or spliceostatin A) as described herein to increase the infectivity of the viral vector and/or to increase the expression of a polypeptide or RNA (e.g., an mRNA, non-coding RNA, shRNA, miRNA, crRNA, or trans-acting crRNA) encoded by the viral vector. For example, human islet cells, cardiomyocytes, hepatocytes, fibroblasts, cancer cells, neuronal cells, stem cells or muscle cells can be exposed to both a viral vector and one or more spliceosome inhibitors (e.g., meayamycin B or E7107) as described herein to increase the infectivity of the viral vector and/or to increase nucleic acid expression from the viral vector. In some cases, isolated human islet cells from a diabetic patient can be treated with a viral vector (e.g., an AAV vector) and one or more spliceosome inhibitors (e.g., meayamycin B or E7107) ex vivo and then transplanted into the diabetic patient. In such a case, the viral vector (e.g., an AAV vector) can be designed to drive expression of a GLP-1 polypeptide.

In some cases, one or more spliceosome inhibitors (e.g., meayamycin B or E7107) can be administered to a mammal before, together with, or after administration of an AAV designed to express a polypeptide (e.g., a heterologous polypeptide) or nucleic acid (e.g., a heterologous RNA). In such cases, increased AAV infectivity or increased polypeptide or nucleic acid expression from the viral vector can occur within the mammal as compared to the level of AAV infectivity or expression that occurs in a comparable mammal in the absence of administration of the one or more spliceosome inhibitors.

In some cases, a viral vector described herein can be administered to a mammal (e.g., a human) in a biologically compatible solution or a pharmaceutically acceptable delivery vehicle. Suitable pharmaceutical formulations depend in part upon the use and the route of entry, e.g., transdermal or by injection. Such forms should not prevent the composition or formulation from reaching target cells (e.g., islet cells, immune cells, or tumor cells) or from exerting its effect. For example, pharmacological compositions injected into the blood stream should be soluble.

While dosages administered can vary from patient to patient (e.g., depending upon desired response or the disease state), an effective dose can be determined by setting as a lower limit the concentration of virus proven to be safe and escalating to higher doses, while monitoring for the desired response (e.g., heterologous polypeptide expression from the viral vector) along with the presence of any deleterious side effects. As described herein, the use of one or more spliceosome inhibitors (e.g., meayamycin B or E7107) can allow for the use of a reduced viral vector dose as compared to the dose needed to achieve the same viral vector infectivity and/or expression when spliceosome inhibitors are not used. In some cases, the viral vectors (e.g., AAV vectors) provided herein can be delivered in a dose ranging from, for example, about $10^8$ genome copies per kg (gc/kg) to about $10^{14}$ gc/kg.

The invention will be further described in the following examples, which do not limit the scope of the invention described in the claims.

EXAMPLES

Example 1

Inhibiting Post-entry Restriction of AAV Vectors

Figure 2:
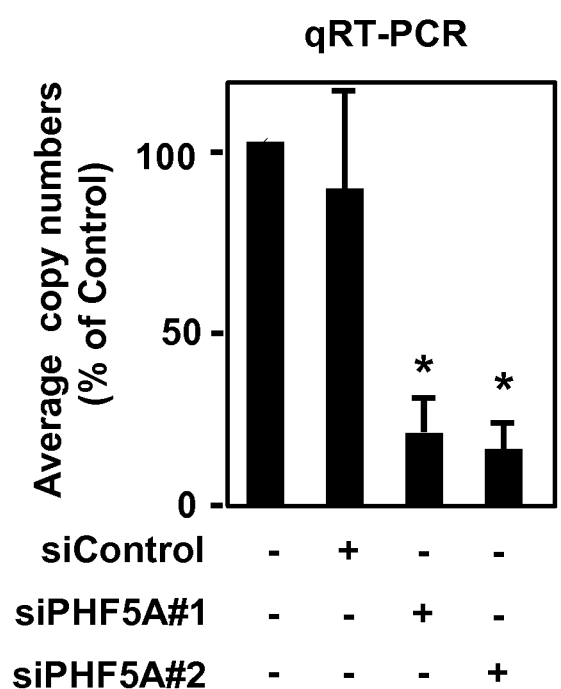
FIG. 2 contains graphs plotting the levels of PHF5A transcripts in HeLa cells treated with control or PHF5A siRNAs at 48 hours. The levels were determined by quantitative RT-PCR.
Figure 3:
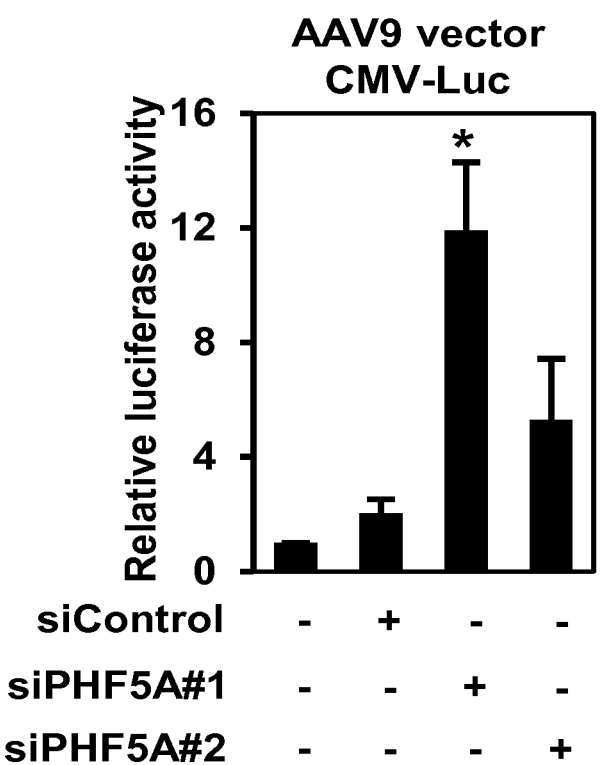
FIG. 3 contains graphs plotting the relative light units for luciferase expression from HeLa cells exposed to luciferase-expressing AAV9 vectors. HeLa cells were transfected with control or PHF5A siRNAs for 24 hours, followed by infection with AAV9 CMV-Luc vectors for an additional 48 hours. The luciferase assay was performed to determine relative luciferase activities in treated cells. Data are shown as averages of three independent experiments with error bars representing standard error of the mean. *=p<0.05.
Figure 4:
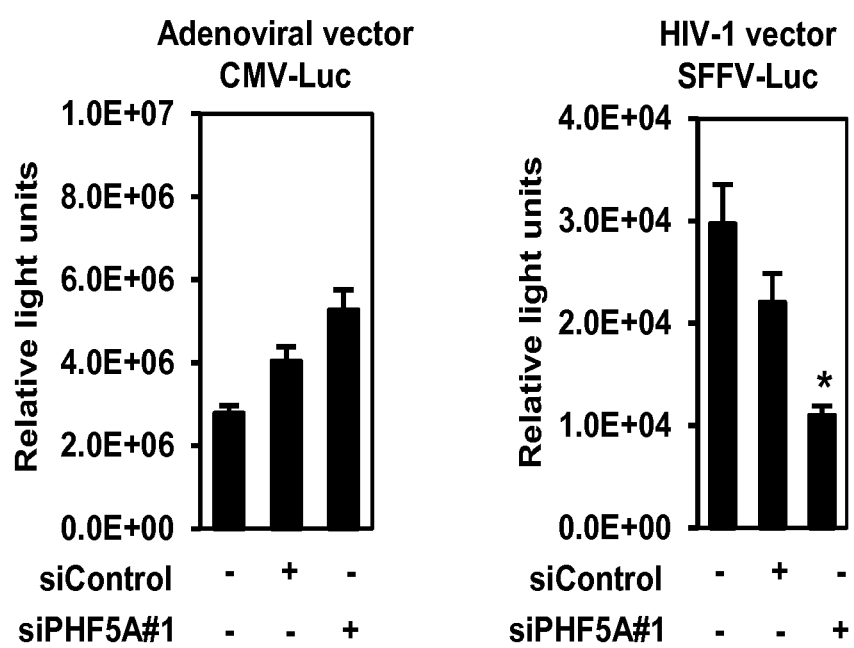
FIG. 4 contains graphs plotting the relative light units for luciferase expression from HeLa cells exposed to luciferase-expressing adenoviral and HIV-1-based lentiviral vectors. HeLa cells were transfected with control or PHF5A siRNAs for 24 hours, followed by infection with the vectors for an additional 48 hours. Data are shown as averages of three independent experiments with error bars representing standard error of the mean. *=p<0.05.

Through screening of the siRNA library, 12 candidate genes were identified (FIG. 1). Disruption of those genes in HeLa cells increased luciferase expression by an AAV9 vector, AAV9 CMV-Luc, over 10-fold (FIG. 1). Treatment of HeLa cells with two PHF5A siRNAs led to over 80% reduction in PHF5A transcripts (FIG. 2) and increased the transduction by AAV9 vectors up to 12-fold (FIG. 3). In contrast, disruption of PHF5A expression did not strongly enhance transgene expression of luciferase-encoding adenoviral or HIV-based lentiviral vectors (FIG. 4). These results suggest that PHF5A plays a role in restricting AAV vector transduction.

Figure 5:
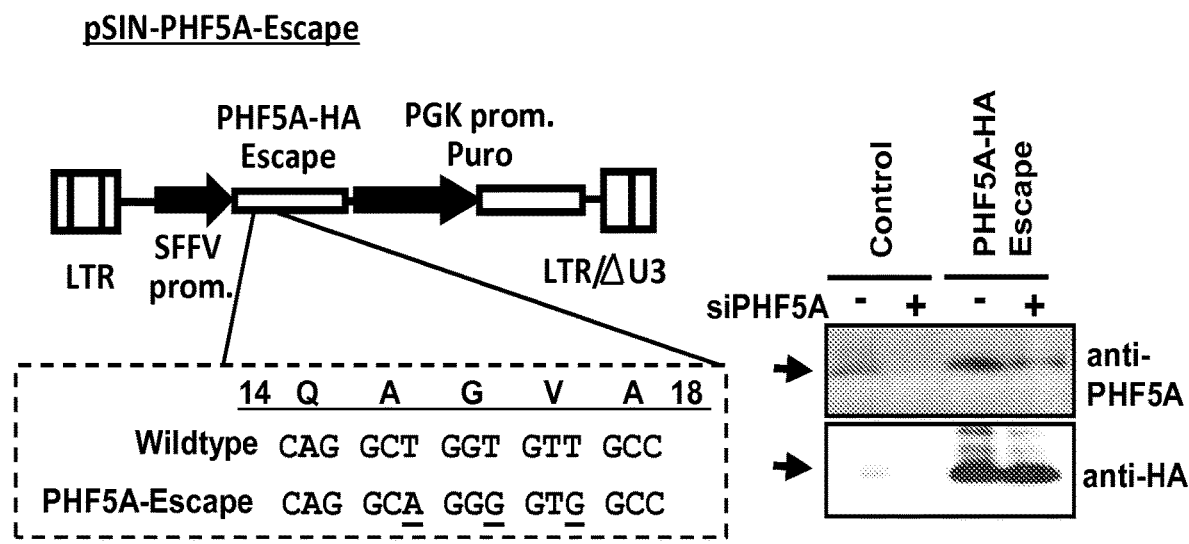
FIG. 5 contains a schematic of the lentiviral vector pSIN-PHF5A-Escape with the PHF5A-HA Escape transgene, generated through introduction of three silent mutations in the PHF5A siRNA #1-targeted sequence. Western blotting was performed to verify the expression of the PHF5A-HA-Escape and its resistance to the PHF5A siRNA #1 treatment. Anti-PHF5A antibody was used to detect endogenous and over-expressed PHF5A-HA, while anti-HA antibody detected the HA-tagged PHF5A. The "QAGVA" sequence is set forth in SEQ ID NO:1, the "CAG GCT GGT GTT GCC" sequence is set forth in SEQ ID NO:2, and the "CAG GCA GGG GTG GCC" sequence is set forth in SEQ ID NO:3.
Figure 6:
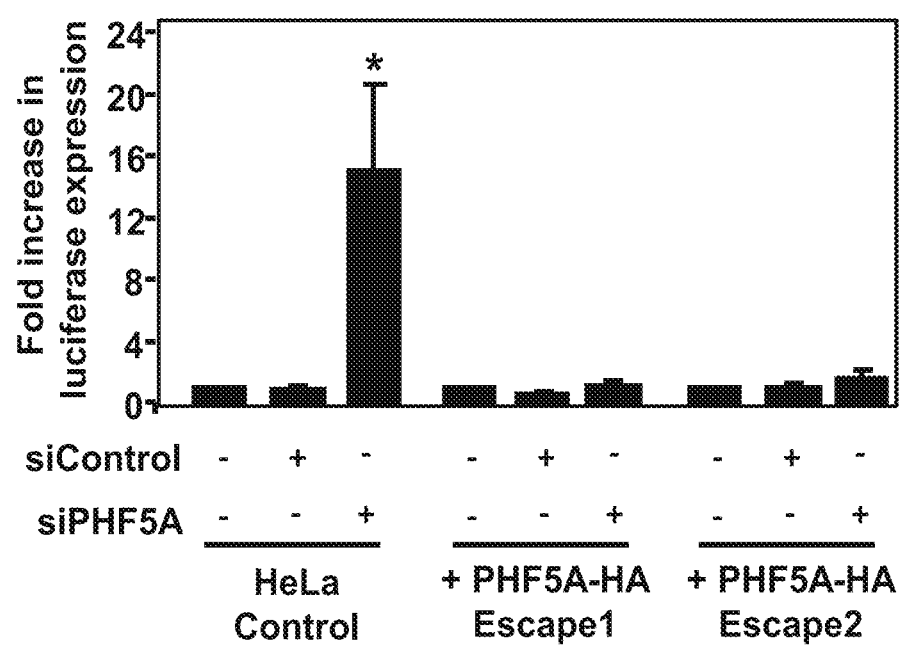
FIG. 6 contains graphs plotting the relative light units for luciferase expression form HeLa cell lines stably expressing the PHF5A-HA-Escape mutant. HeLa cell lines were generated through lentiviral transduction of the escape mutant, followed by puromycin selection. Upon treatment with the PHF5A siRNA and AAV9 CMV-Luc vector, luciferase expression was determined in control HeLa and PHF5A-HA-Escape-expressing HeLa cells. Data are shown as averages of three independent experiments with error bars representing standard error of the mean. *=p<0.05.

To rule out possible off-target effects of siRNA, a lentiviral vector expressing an siRNA-resistant, HA-tagged PHF5A mutant, PHF5A-HA-Escape, was generated through introduction of three silent mutations in the siRNA recognition site (FIG. 5). Upon lentiviral transduction and puromycin selection, two independent HeLa cell lines with stable PHF5A-HA Escape expression were established. Western blot analysis with anti-PHF5A and anti-HA antibodies verified that PHF5A-HA-Escape was resistant to the specific siRNA treatment (FIG. 5, right panel). When endogenous PHF5A expression was disrupted by the PHF5A siRNA, enhanced AAV9 vector transduction was observed in control HeLa cells, but not in HeLa cells over-expressing the siRNA-resistant PHF5A (FIG. 6). These data demonstrate that the enhanced AAV9 vector transduction by the PHF5A siRNA is PHF5A-specific but not due to off-target effects. Thus, subsequent studies were focused on the role of PHF5A in AAV vector transduction.

Figure 7:
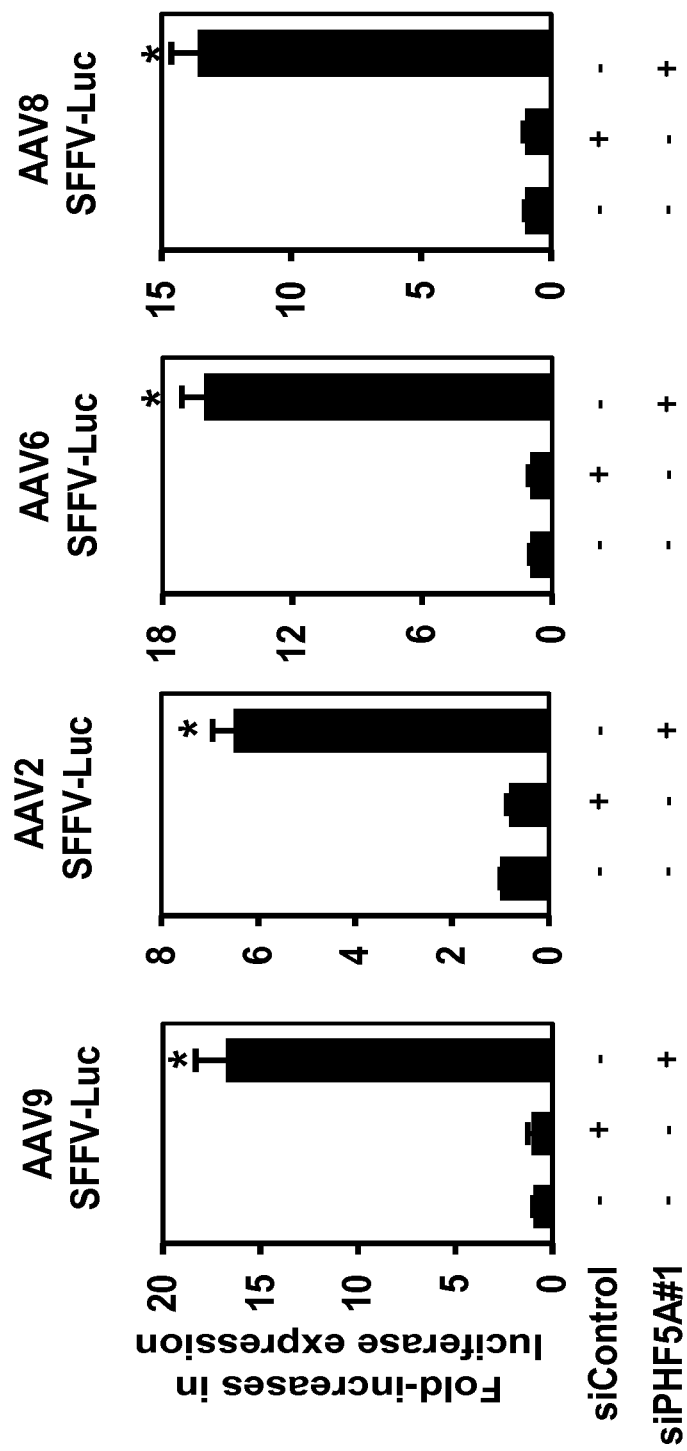
FIG. 7 contains graphs plotting the fold-increases in luciferase expression from HeLa cells exposed to the indicated AAV vectors. HeLa cells pre-treated with control or PHF5A siRNAs for 24 hours were transduced with AAV9, 2, 6, or 8 vectors expressing luciferase under the control of the SFFV retroviral promoter with no splicing unit. Relative increase in luciferase expression was determined 48 hours post infection (p.i.). Averages of three independent experiments were shown. Error bars represent standard error of the mean.
Figure 8:
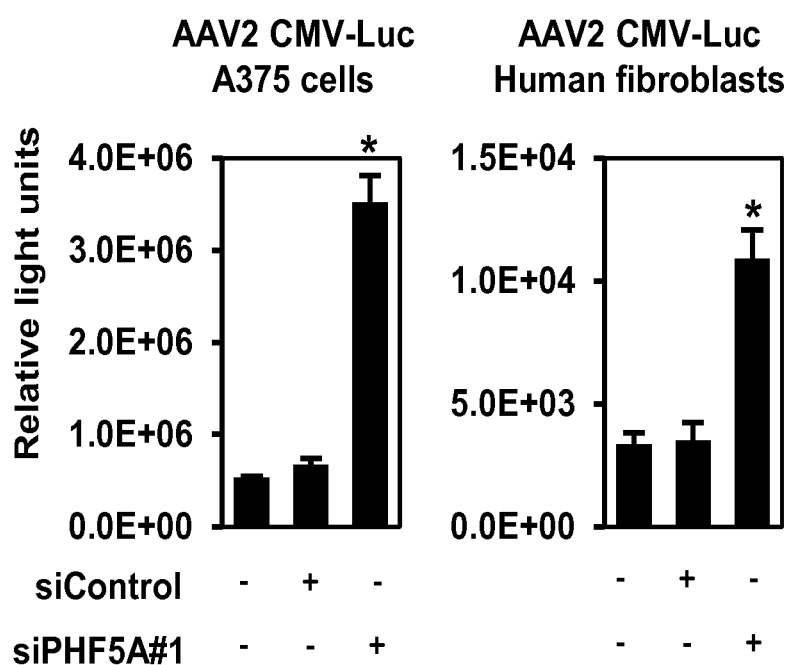
FIG. 8 contains graphs plotting the relative light units for luciferase expression from melanoma A375 cells and primary human fibroblasts exposed to the indicated AAV vectors. Melanoma A375 cells and primary human fibroblasts were pre-treated with siRNAs for 24 hours, followed by transduction with the AAV2 CMV-Luc vector for 48 hours.

To rule out the possibility of PHF5A modulating the CMV promoter activity, the CMV internal promoter in the AAV vector genome was replaced with a retroviral SFFV promoter lacking an additional splicing unit. Similar increases in AAV9 vector transduction were observed upon disruption of PHF5A (FIG. 7). When the effects of PHF5A knockdown were evaluated on the transduction of AAV vectors with serotypes 2, 6 and 8 capsids, a 6, 16 and 14-fold increase in luciferase expression, respectively, was observed (FIG. 7). Thus, the PHF5A-mediated restriction was independent from internal promoters or receptors used by AAV vectors. Likewise, knocking down PHF5A was effective at increasing AAV vector transduction in other cell types, including A375 melanoma cells and primary cardiac fibroblasts (FIG. 8).

Figure 9:
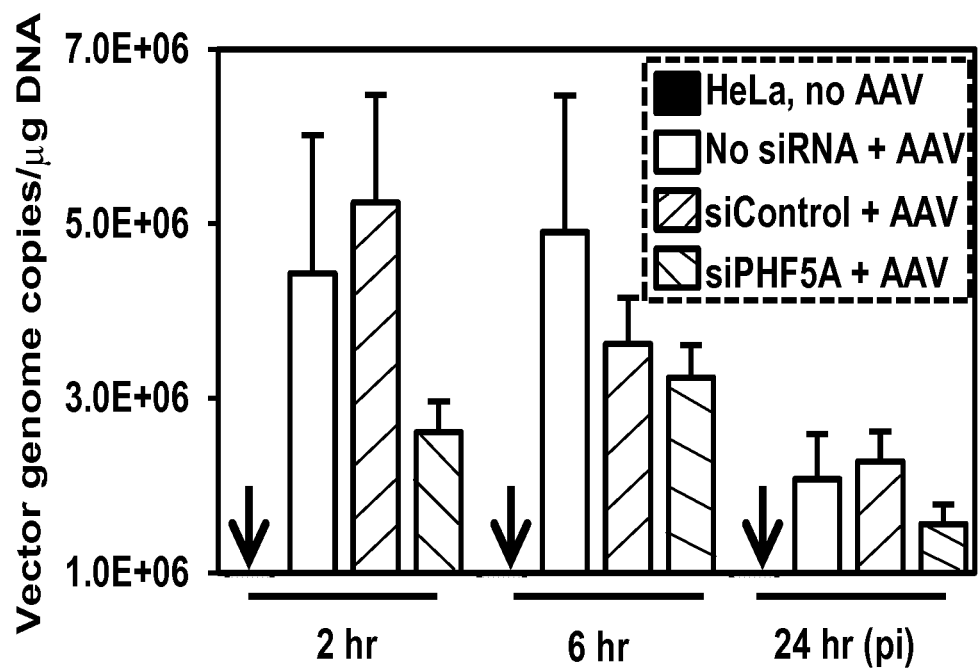
FIG. 9 is a graph plotting the vector copies per µg DNA in the nucleus or cytoplasm for HeLa cells exposed to AAV vectors. HeLa cells were pre-treated with siRNAs for 24 hours and infected by the AAV9 CMV-Luc vector. Total nuclear DNA was isolated and AAV vector genome copies were determined by quantitative real-time PCR at 2, 6, and 24 hours p.i. All samples were prepared in duplicate, and results represent the average of three separate experiments.
Figure 10:
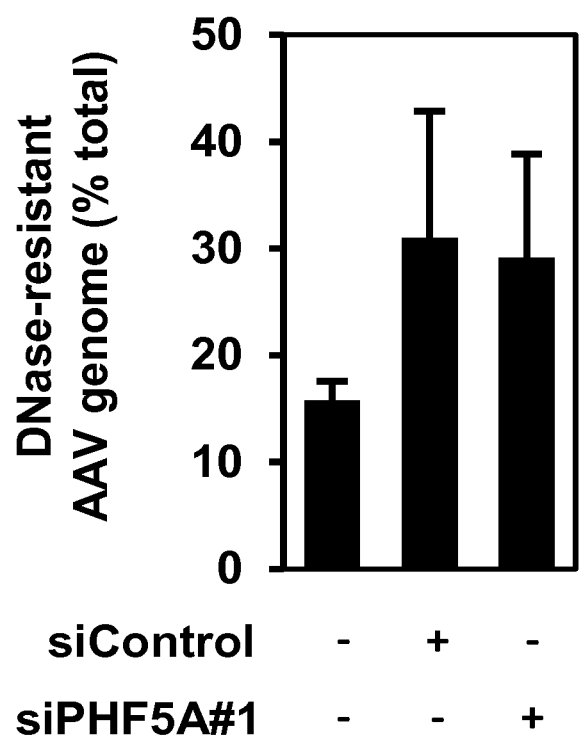
FIG. 10 is a graph plotting the percent DNase-resistant AAV genomes. HeLa cells were pre-treated with siRNAs for 24 hours and infected by the AAV9 CMV-Luc vector. Total and DNase-resistant AAV genome copies at 6 hours p.i. were determined to assess the percent DNase-resistant AAV genomes. Samples were in duplicate, and results show the average of two independent experiments.
Figure 11:
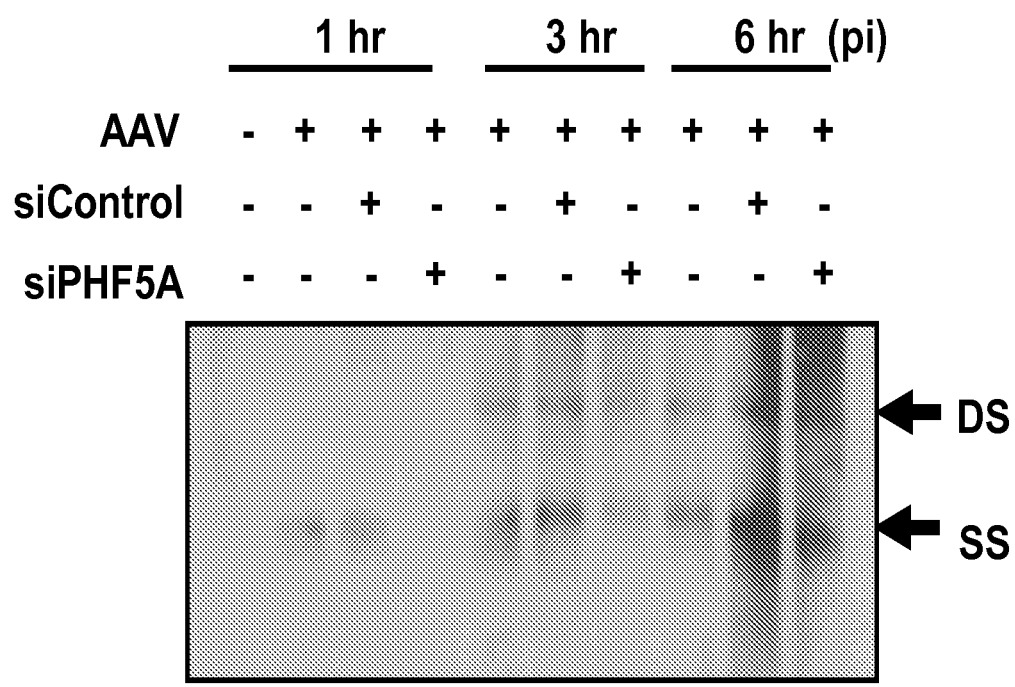
FIG. 11 contains photographs of the Southern blotting demonstrating the single-and double-stranded AAV vector genome monomers. siRNA-treated HeLa cells were infected with AAV9 CMV-Luc vector for 1, 3, or 6 hours. Total nuclear DNA samples were used to detect the vector-derived single-stranded and double stranded monomers by Southern blotting.
Figure 12:
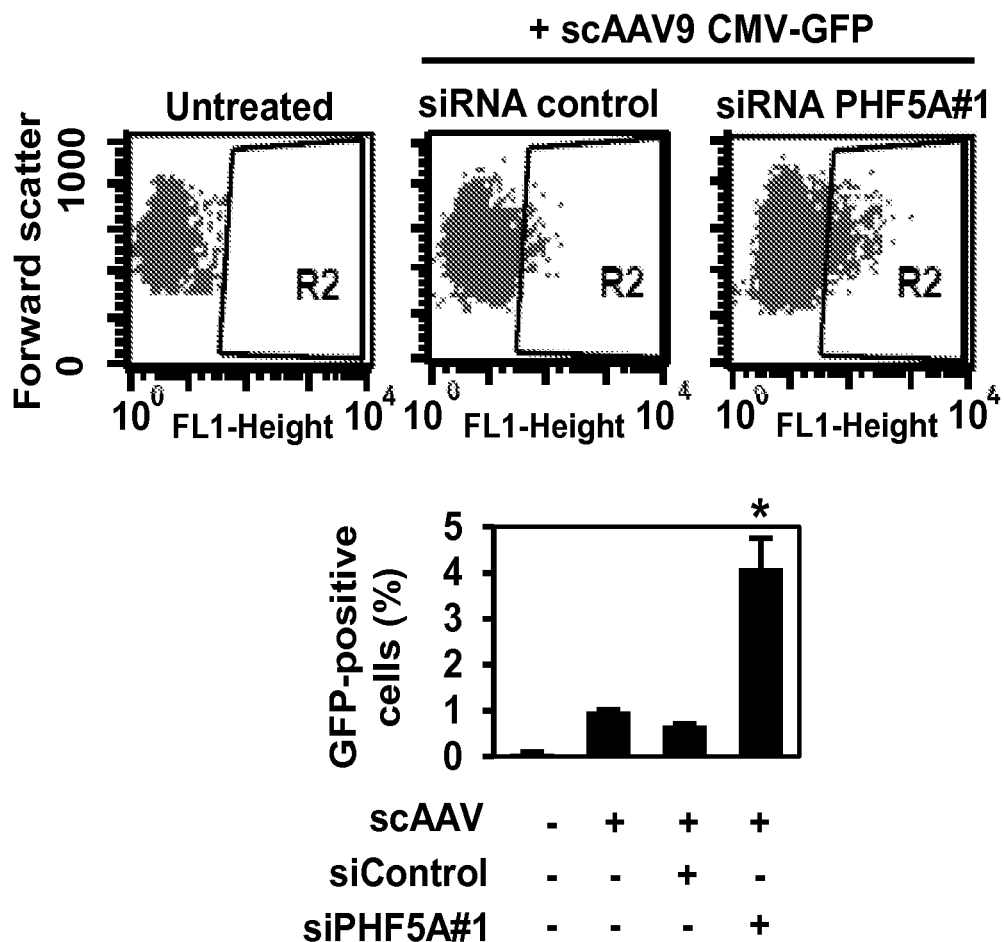
FIG. 12 contains flow cytometry data plotting the infectivity of a GFP-expressing self-complementary (sc) AAV9 vector upon disruption of PHF5A by the siRNA. HeLa cells were transfected with siRNAs for 24 hours, followed by infection with a GFP-expressing scAAV9 vector for 48 hours. Flow cytometry analysis was performed to quantify GFP-positive cell populations. The graph represents percentage of GFP-positive cells from the R2-gated population.
Figure 13:
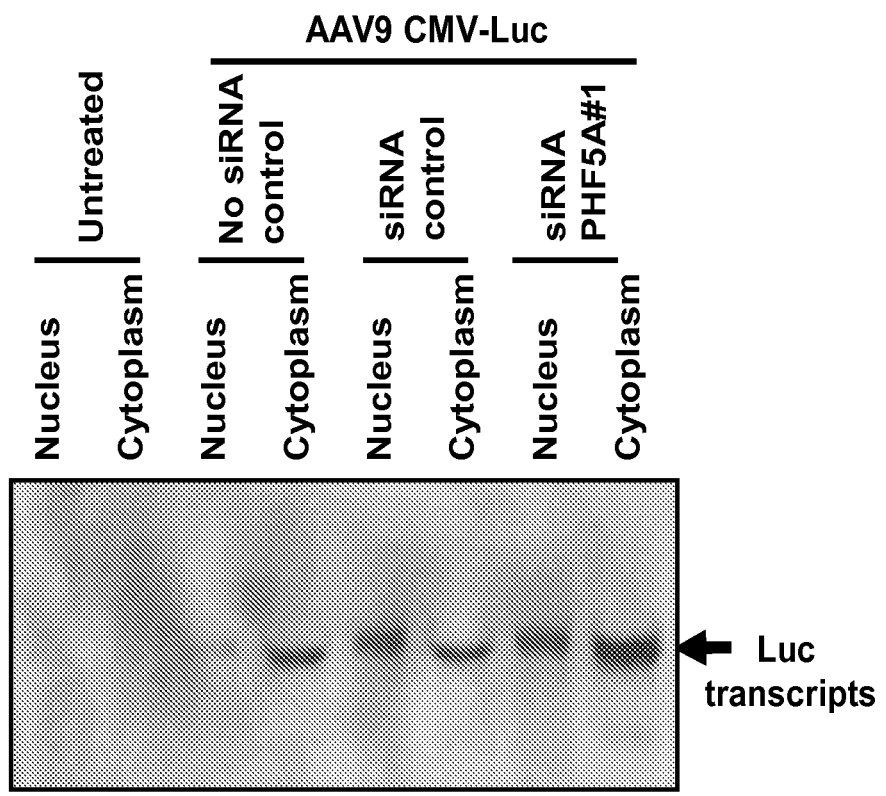
FIG. 13 is a photograph of a northern blot analysis for luciferase RNA in HeLa cells exposed to AAV9 vectors upon disruption of PHF5A. HeLa cells were pre-treated or untreated with siRNAs for 24 hours, followed by transduction with the AAV9 CMV-Luc vector for 36 hours. Nuclear and cytoplasmic RNA samples were subject to the Northern blotting analysis for detection of the luciferase transcripts.

Next, the influence of PHF5A ablation on nuclear entry by AAV vectors was examined Nuclear DNA was isolated at 2, 6 and 24 hours after AAV9 vector infection of HeLa cells pretreated with control or the PHF5A siRNA. When compared with control HeLa cells, slightly reduced AAV genomic DNA in the nucleus of cells was found with PHF5A disruption (FIG. 9). At each time point, there were comparatively large quantities of AAV in the nucleus of untreated HeLa cells versus cells treated with the PHF5A siRNA. These results demonstrate that PHF5A does not block the nuclear entry of AAV vectors. The uncoating efficiency of AAV vector genome upon PHF5A disruption was then examined. In HeLa cells treated with control or PHF5A siRNAs, approximately 30% of total AAV DNA detected was DNase-resistant at 24 hours post infection (p.i.) (FIG. 10), suggesting that PHF5A does not affect uncoating process of AAV vectors. The effects of PHF5A ablation on the second strand synthesis of AAV vectors also was examined (FIG. 11). Southern blot analysis demonstrated that the single-stranded (ss) monomer form was predominant at 1 hour p.i., while both ss and double-stranded (ds) monomer forms were observed at 3 and 6 hours p.i. No notable increase in double-stranded monomers was found in HeLa cells pretreated with the PHF5A siRNA, suggesting that PHF5A does not affect the second strand synthesis of AAV vectors. To further verify this, the influence of PHF5A disruption on transduction by a self-complementary AAV (scAAV) vector was tested. This does not rely on second-strand synthesis for transgene expression (FIG. 12). Upon transduction with the GFP-expressing scAAV vector packaged by AAV9 capsid, significant increases in GFP transduction in HeLa cells treated with the PHF5A siRNA were observed. Silencing of PHF5A increased the number of GFP-positive cells as well as the fluorescent intensity of GFP-positive cell populations (FIG. 12). These results indicate that PHF5A blocks the process of AAV vector transduction after second-strand synthesis. The effects of PHF5A disruption on the transcription of AAV9 CMV-Luc vector were then explored. Northern blot analysis showed that pretreatment with the PHF5A siRNA increased the levels of luciferase-specific transcripts in HeLa cells at 36 hours p.i. (FIG. 13), suggesting that PHF5A affects the step before translation. Together, these results demonstrate that PHF5A acts to restrict AAV vector transduction somewhere between AAV second-strand synthesis and the transcription of the AAV vector transgene. It also appears that PHF5A does not directly target AAV vector genome.

Figure 14:
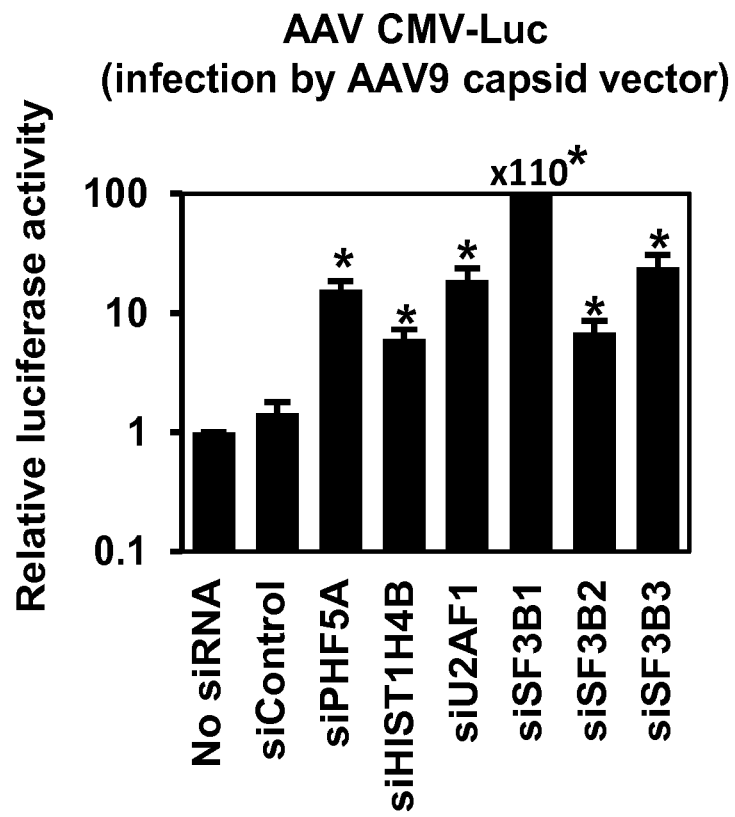
FIG. 14 contains graphs plotting the relative light units for luciferase expression from HeLa cells exposed to a luciferase-expressing AAV9 vector and treated by specific siRNAs targeting the PHF5A-interacting factors. HeLa cells were transfected with control siRNA, or siRNAs targeting PHF5A, histone 4, U2AF1, SF3B1, SF3B2, and SF3B3 for 24 hours, followed by the AAV9 CMV-Luc vector transduction. Relative luciferase expression was determined 48 hours p.i.
Figure 15:
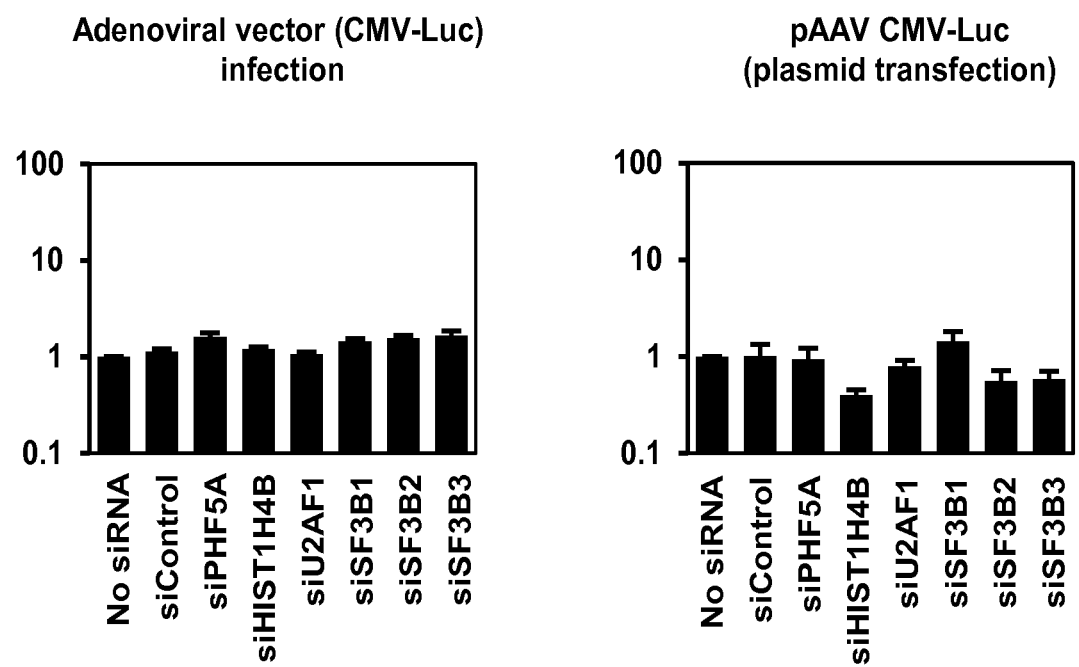
FIG. 15 contains graphs plotting the relative light units for luciferase expression from HeLa cells exposed to luciferase-expressing adenoviral vector, or transfected with a pAAV-CMV-Luc plasmid. HeLa cells were transfected with control siRNA, or siRNAs targeting PHF5A, histone 4, U2AF1, SF3B1, SF3B2, and SF3B3 for 24 hours, followed by transduction with a luciferase-expressing adenoviral vector, or transfection with the vector genome plasmid, pAAV CMV-Luc for 48 hours. This plasmid was used to generate the infectious AAV9 CMV-Luc vector, packaged by AAV9 capsid, used in FIG. 13.

PHF5A was reported to interact with various proteins, including the U2 snRNP proteins, SF3B1, SF3B2, SF3B3, and U2 snRNP-associated factor U2AF1 (Hubert et al., *Genes Dev.*, 27:1032-1045 (2013); Rzymski et al., *Cytogenet. Genome Res.*, 121:232-244 (2008); and Wang et al., *Mol. Cell. Biol.*, 23:7339-7349 (2003)). To further understand the underlying mechanism of the PHF5A-mediated block of AAV vector transduction, the effects of disrupting those proteins on AAV vector transduction were assessed. Specific siRNA-treated cells were infected with AAV9 CMV-Luc vectors at 24 hours post transfection, with luciferase activity assayed 48 hours p.i. Ablation of U2 snRNP components (SF3B1, SF3B2, SF3B3) and U2AF1 resulted in a substantial increase in luciferase activity relative to HeLa cells pre-treated with a control siRNA (FIG. 14). Upon infection with a luciferase-expressing adenoviral vector, no increase in luciferase activity was seen in HeLa cells with disrupted U2 snRNP proteins (FIG. 15, left panel). Furthermore, disruption of U2 snRNP components or U2AF1 did not enhance the luciferase expression from a transfected AAV vector plasmid, pAAV CMV-Luc (FIG. 15, right panel). These results suggest that PHF5A blocks AAV vector transduction through an interaction with U2 snRNP proteins and U2AF1, and that the introduction of AAV vector genome by AAV vector infection was essential for the U2 snRNP-mediated restriction of AAV vector transduction.

Taken together, these results confirm the identification of PHF5A as a factor responsible for post-entry restriction of AAV vector transduction. Transduction efficiencies of HIV-1 and adenoviral vectors with the same promoters were not affected by suppression of PHF5A. PHF5A appeared to block AAV vector transduction after the DNA second strand synthesis before transcription. In addition, disruption of other U2 snRNP components enhanced AAV vector infectivity. These results also demonstrate that inhibitors of U2 snRNP can be used to enhance AAV vector infectivity.

Example 2

Pharmacological U2 snRNP Inhibition

Figure 16:
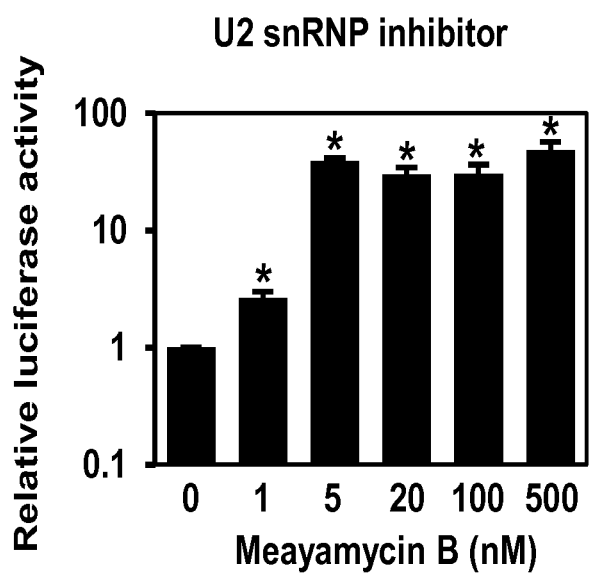
FIG. 16 is a graph plotting the relative luciferase activity in Hela cells treated with increasing doses of U2 snRNP inhibitor (meayamycin B), or other splicing inhibitors (Isoginkgetin and 3-aminophenylboronic acid). HeLa cells were treated with indicated concentrations of U2 snRNP inhibitor (meayamycin B) followed by transduction with the AAV9 CMV-Luc vector 3 hours post drug treatment. Relative luciferase expression was determined 48 hours p.i.
Figure 17:
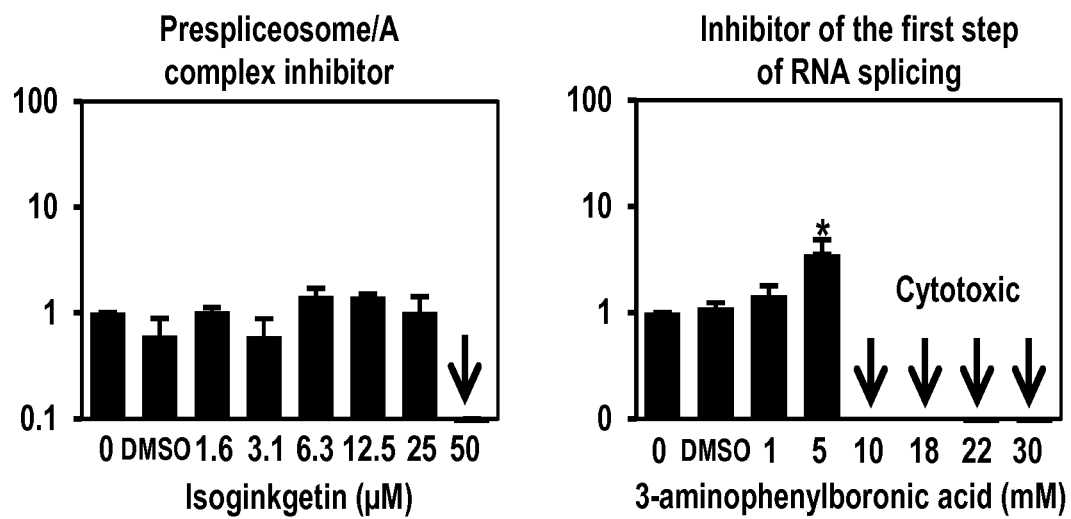
FIG. 17 contains graphs plotting the relative luciferase activity in Hela cells treated with increasing doses of general splicing inhibitors (Isoginkgetin and 3-aminophenylboronic acid). HeLa cells were treated with indicated concentrations of Isoginkgetin or 3-aminophenylboronic acid, followed by transduction with the AAV9 CMV-Luc vector 3 hours post drug treatment. Relative luciferase expression was determined 48 hours p.i.

The following was performed to test the ability of a specific SF3b inhibitor, meayamycin B, to enhance AAV vector infectivity. When HeLa cells were pre-treated with this drug at an increasing dose 3 hours before AAV9 vector infection, dose-dependent increases (up to 49-fold) in relative luciferase activity were seen (FIG. 16, left panel). Other splicing inhibitors, including isoginkgetin, which blocks recruitment of U4/U5/U6 snRNPs during splicing (Schneider-Poetsch et al., *Nat. Chem. Biol.*, 6:189-198 (2010)), and 3-Aminophenylboronic acid, an inhibitor of the initial step of pre-mRNA processing, did not show notable increases in AAV vector transduction (FIG. 17). This indicates that U2 snRNP and associated PHF5A and U2AF1, but not the general splicing process, plays a key role in the prevention of AAV vector transduction.

Figure 18:
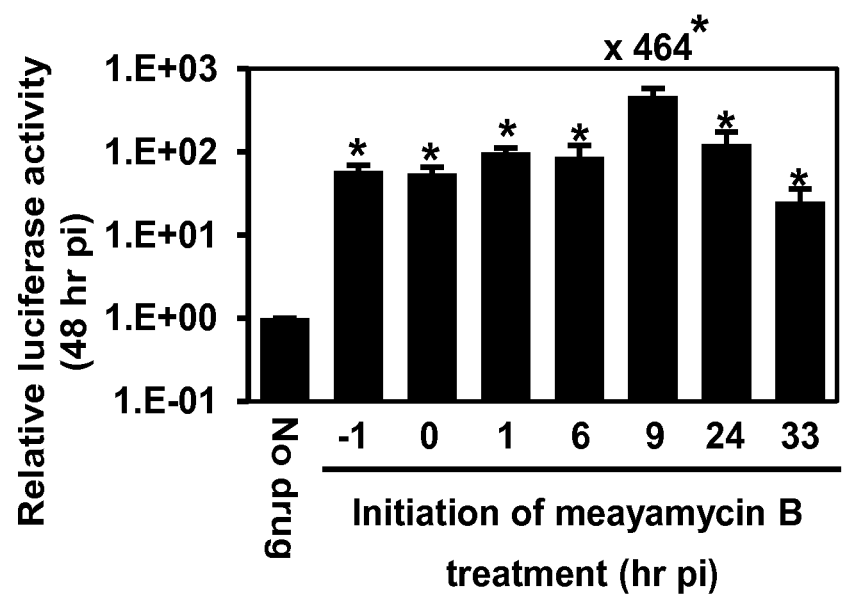
FIG. 18 is a graph plotting the relative luciferase activity in HeLa cells treated with meayamycin B (20 nM) at various time points before or after a luciferase-expressing AAV9 vector infection as indicated. Relative luciferase expression was determined 48 hours p.i.
Figure 19:
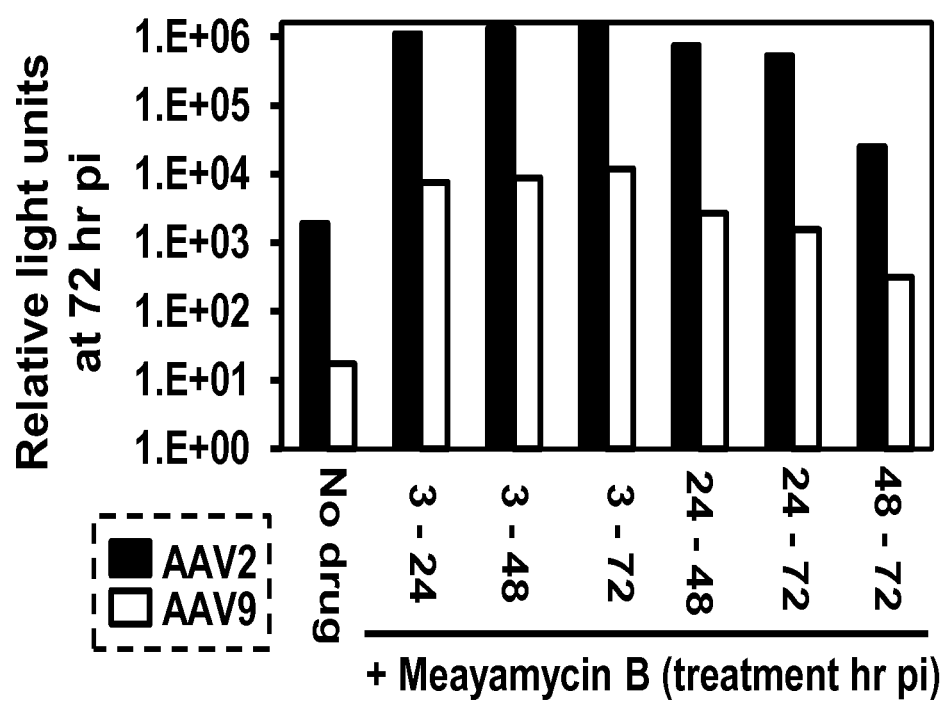
FIG. 19 contains a graph plotting the relative luciferase activity in HeLa cells treated with luciferase-expressing AAV2 or AAV9 vectors, followed by 20 nM meayamycin B treatments at various time points (3-24, 3-48, 3-72, 24-48, 24-72, or 48-72 hours p.i.). Relative luciferase expression was determined 72 hours p.i.
Figure 20:
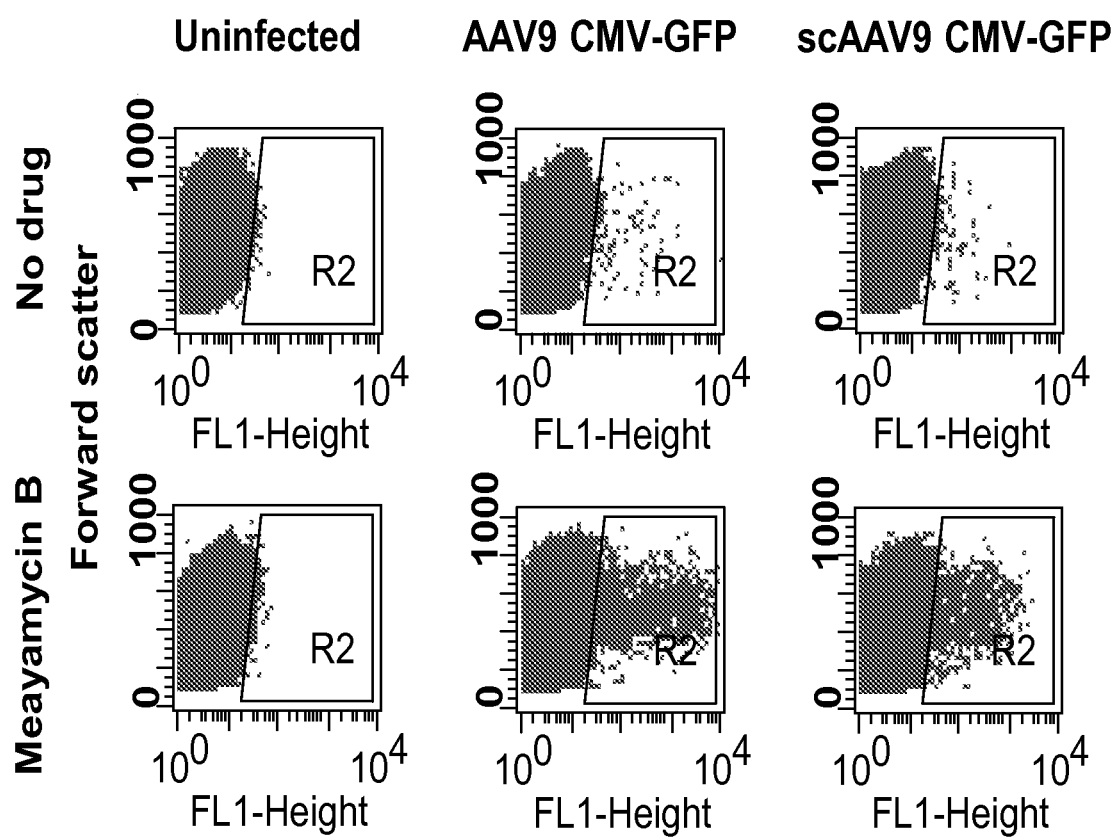
FIG. 20 contains flow cytometry data plotting the infectivity of GFP-expressing single-stranded AAV9 or self-complementary (sc) AAV9 vectors. HeLa cells were infected by AAV9 CMV-GFP or scAAV9 CMV-GFP vectors, followed by treatment with 20 nM meayamycin B at 8 hours p.i. Flow cytometry analysis was performed to observe GFP-positive cell populations at 48 hours p.i.

To understand the mechanism of U2 snRNP-mediated block of AAV vector transduction, the optimal timing of meayamycin B treatment in relationship to AAV infection was further assessed. Pretreatment with the drug was not needed in order for it to enhance AAV9 infection (FIG. 18). The largest increase in relative luciferase activity (464-fold) was observed when cells were treated by 20 nM meayamycin B, 9 hours post AAV9 vector infection. In contrast, treatment at 33 hours post p.i. exhibited relatively weak effects. To further map the optimal timing of U2 snRNP inhibition for AAV vector transduction, AAV2 and AAV9 vector-infected HeLa cells were treated with 5 nM meayamycin B at various time points and duration, and luciferase activity was assessed at 3 days p.i. Treating with meayamycin B 3 hours p.i. and washing cells 1, 2 or 3 days after receiving the drug resulted in similarly high levels of enhanced luciferase expression (FIG. 19, up to 380- and 359-fold increases in AAV2 and AAV9 vector transduction, respectively). Washout of meayamycin B for 48 hours after 3-24 hours of treatment did not strongly compromise its effects on AAV vector transduction. In contrast, the effects of meayamycin B on AAV vector transduction were impaired when drug was added either 24 or 48 hours p.i. (FIG. 19). Thus, optimal enhancement of AAV vector transduction involved initiation of U2 snRNP inhibition prior to 24 hours post AAV vector infection. This indicates that U2 snRNP blocks AAV vectors at a particular post-entry step of viral infection, likely occurring before 24 hours p.i. When the effects of meayamycin B were assessed on GFP-expressing vectors, meayamycin B enhanced the transduction by both single-stranded and self-complementary AAV vectors through increasing the number as well as the fluorescent intensity of GFP-positive cells (FIG. 20).

Figure 21:
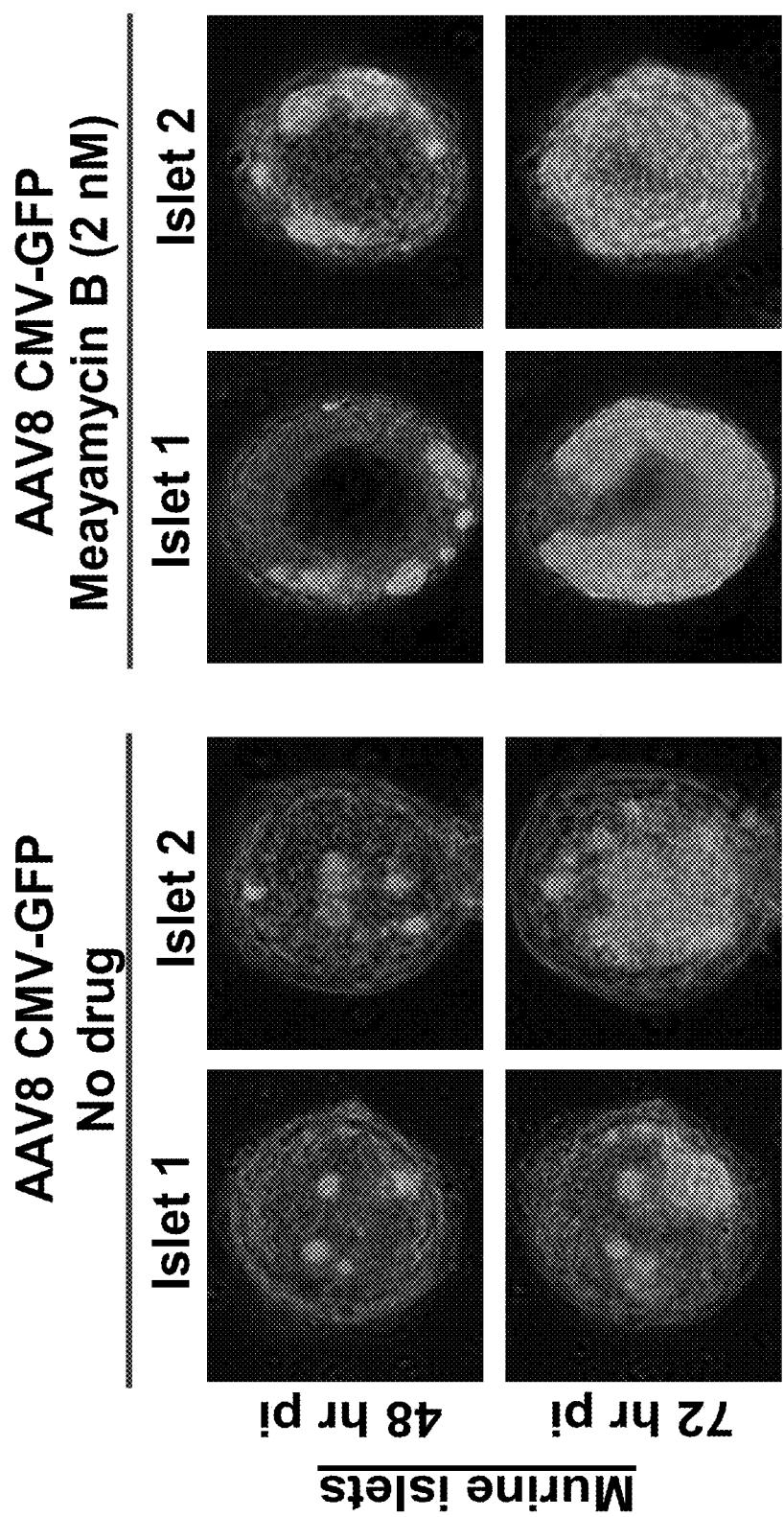
FIG. 21 contains photographs of murine islet cells exposed to AAV8-GFP vectors along with meayamycin (2 nM). Images of GFP expressing islets were taken at two and three days post infection.
Figure 22:
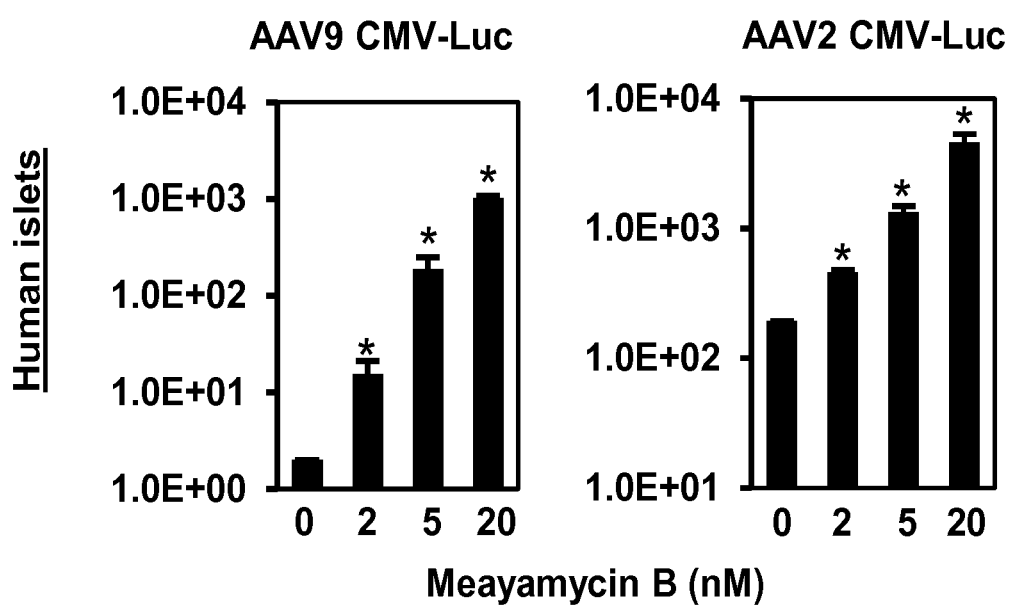
FIG. 22 contains graphs plotting relative light units in human islet cells 48 hours post infection with an AAV2 or AAV9 vector and following treatment with the indicate amount of meayamycin at 7 hours post infection. Luciferase expression was analyzed 48 hours p.i.
Figure 23:
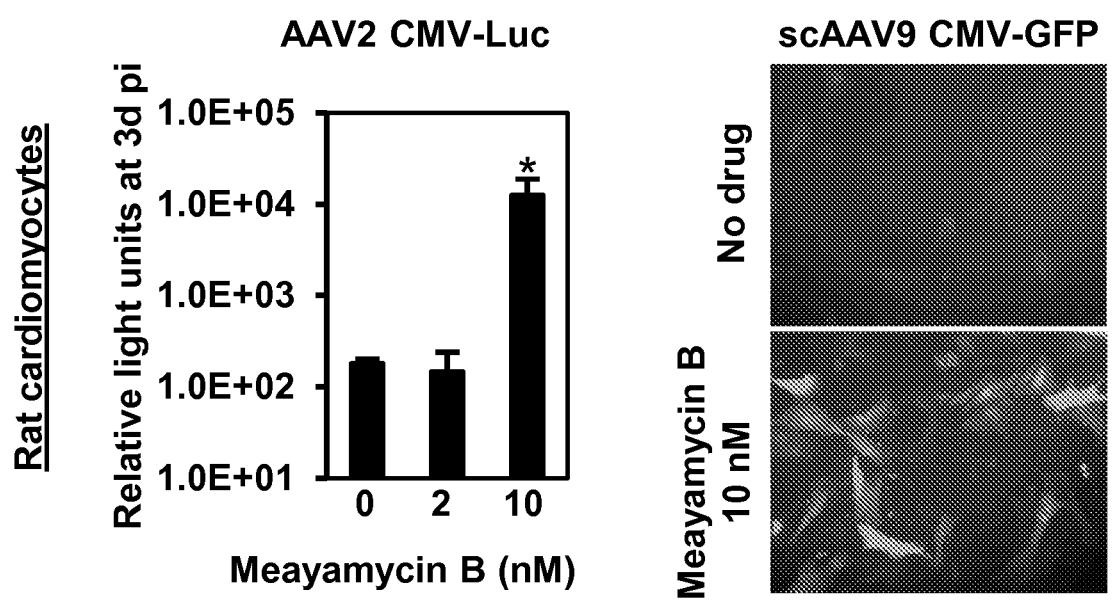
FIG. 23 presents a graph plotting the relative luciferase activity and images of GFP-expressing cells in neonatal rat cardiomyocytes. Primary cardiomyocytes were infected with AAV2 CMV-Luc or scAAV9 CMV-GFP vectors and treated with meayamycin B, 3 hours p.i. Luciferase activity was measured 3 days p.i., while GFP expression was monitored at 5 days p.i.
Figure 24:
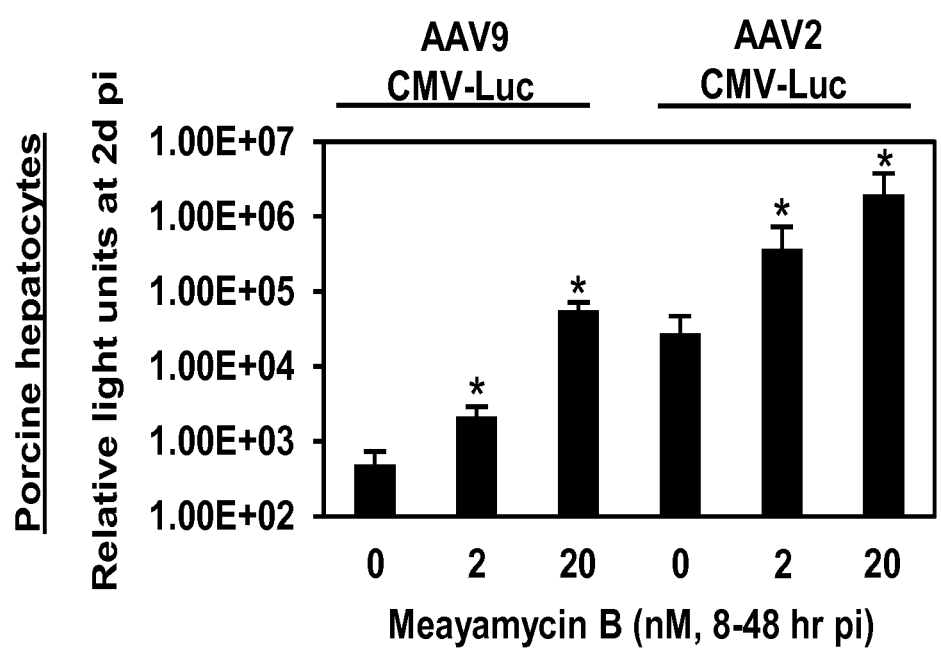
FIG. 24 contains graphs plotting the relative luciferase activity in porcine hepatocytes exposed to AAV2 or AAV9 CMV-Luc vectors. Cells were infected with AAV vectors for 8 hours, virus was then removed, and cells were treated with 0, 2, or 20 nM meayamycin B. Cells were harvested 48 hours p.i. for the luciferase assay.

The ability of meayamycin B to boost AAV transduction in various cell types, relevant to gene therapy applications, was also tested. First, primary pancreatic islets were isolated from 8 week-old C57B1/6 mice, which were then transduced with AAV8 CMV-GFP and treated with 2 nM meayamycin B 3 hours p.i. Cells were monitored by BioStation Live Imaging for three days. There were increased numbers of GFP expressing cells in drug treated mouse islets as compared to the control islets 48 and 72 hours p.i. (FIG. 21). The effects of meayamycin B on primary human pancreatic islets were then tested. Cells were infected with AAV2 or AAV9 CMV-Luc vectors and treated with 0, 2, 5, or 20 nM meayamycin B at 7 hours p.i. When luciferase expression was monitored at 48 hours p.i., a dose-dependent increase in luciferase expression in AAV2 and AAV9 infected cells (up to 44- and 24-fold increases in AAV9 and AAV2 transduction) was observed (FIG. 22). The effects on neonatal rat cardiomyocytes were tested next. Primary cardiomyocytes were infected with AAV2 CMV-Luc, followed by 0, 2, or 10 nM meayamycin B treatments at 3 hours post infection for 3 days. Although 2 nM meayamycin B did not strongly improve vector transduction, 10 nM meayamycin B treatment strongly increased luciferase expression by 72-fold. Using 10 nM meayamycin on neonatal rat cardiomyocytes infected with scAAV9 CMV-GFP also led to notable increase in GFP expression at 5 days p.i. (FIG. 23). Likewise, meayamycin B treatment increased AAV2 and AAV9 transduction of primary porcine hepatocytes (FIG. 24, up to 57- and 18-fold increases in AAV9 and AAV2 vector transduction). These results demonstrate that meayamycin B enhances AAV vector transduction of a variety of cell types from different host species.

Taken together, these results demonstrate that pharmacological U2 snRNP inhibition by, for example, meayamycin B, increased the vector transduction of cancer cell lines and clinically relevant cell types, including pancreatic islets and hepatocytes up to 1000-fold. Thus, genetic and/or pharmacological inhibition of U2 snRNP can be used to increase AAV vector transduction, which allows for efficient AAV vector gene therapy with reduced vector doses. These results also demonstrate a role for U2 snRNP as a post-entry restriction factor for AAV vector transduction.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for infecting a mammal with an AAV vector, wherein said method comprises administering said AAV vector in the presence of a U2 snRNP spliceosome inhibitor to said mammal, wherein said inhibitor is administered within 12 hours preinfection and within 24 hours post-infection, wherein the dose of the AAV vector in the presence of said U2 snRNP spliceosome inhibitor is lower than the dose of said AAV vector in the absence of said U2 snRNP spliceosome inhibitor.

2. The method of claim 1, wherein said mammal is a human.

3. The method of claim 1, wherein said AAV vector is an AAV1, AAV2, AAV3, AAV4, or AAV5 vector.

4. The method of claim 1, wherein said inhibitor is meayamycin B or E7107.

* * * * *

SEQUENCE LISTING

```
<160> NUMBER OF SEQ ID NOS: 3

<210> SEQ ID NO 1
<211> LENGTH: 5
<212> TYPE: PRT
<213> ORGANISM: Homo sapiens

<400> SEQUENCE: 1

Gln Ala Gly Val Ala
1               5

<210> SEQ ID NO 2
<211> LENGTH: 15
<212> TYPE: DNA
<213> ORGANISM: Homo sapiens

<400> SEQUENCE: 2
caggctggtg ttgcc                                                      15

<210> SEQ ID NO 3
<211> LENGTH: 15
<212> TYPE: DNA
<213> ORGANISM: Artificial Sequence
<220> FEATURE:
<223> OTHER INFORMATION: fragment sequence

<400> SEQUENCE: 3
caggcagggg tggcc                                                      15
```